United States Patent [19]
Chollet et al.

[11] Patent Number: 6,090,750
[45] Date of Patent: *Jul. 18, 2000

[54] HERBICIDAL COMBINATIONS

[75] Inventors: Reynold Chollet, Bottmingen, Switzerland; Luke L. Bozeman, Jupiter, Fla.

[73] Assignee: Novartis AG, Basel, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/814,946

[22] Filed: Mar. 10, 1997

Related U.S. Application Data

[63] Continuation of application No. 08/735,289, Oct. 22, 1996, abandoned.

[30] Foreign Application Priority Data

Mar. 13, 1996 [GB] United Kingdom .................... 9605252

[51] Int. Cl.[7] .......................... A01N 25/32; A01N 37/10; A01N 43/40; A01N 43/42
[52] U.S. Cl. .......................... 504/105; 504/130; 504/138; 504/144; 504/324; 71/DIG. 1
[58] Field of Search ..................................... 504/105, 130, 504/138, 144, 324; 71/DIG. 1

[56] References Cited

U.S. PATENT DOCUMENTS

| | | | |
|---|---|---|---|
| 3,444,192 | 5/1969 | Newcomer | 504/324 |
| 5,023,333 | 6/1991 | Hubele | 546/175 |
| 5,238,604 | 8/1993 | Hazen et al. | 252/356 |
| 5,484,760 | 1/1996 | Bussler et al. | 504/103 |
| 5,665,673 | 9/1997 | Anderson et al. | 504/130 |

FOREIGN PATENT DOCUMENTS

| | | |
|---|---|---|
| 354 201 | 2/1990 | European Pat. Off. . |
| 646315 | 4/1995 | European Pat. Off. . |
| 2129109 | 1/1973 | Germany . |
| 1362886 | 8/1974 | United Kingdom . |
| 9424858 | 11/1994 | WIPO . |

OTHER PUBLICATIONS

EPO Search Report, Application No. EP 97102604 (May 1997).

Gauvrit, et al. Oils for Weed Control: Uses and Mode of Action, 1993, Pesticide Sci., 37, 147–153.

*Primary Examiner*—John Pak
*Attorney, Agent, or Firm*—Michael P. Morris; John D. Peabody, III; William A. Teoli, Jr.

[57] ABSTRACT

The invention discloses a novel method for reducing phytotoxicity of Dicamba to crop plants, which comprises co-applying to the crop plants or to the locus thereof a phytotoxicity reducing effective amount of a quinolinyloxy alkanoic acid derivative together with a herbicidally effective amount of Dicamba and salt forms thereof.

16 Claims, No Drawings

HERBICIDAL COMBINATIONS

This application is a continuation of Ser. No. 08/735,289, filed on Oct. 22, 1996, now abandoned.

The present invention relates to a method of controlling undesired plant growth employing co-application of Dicamba and a quinolinyloxy alkanoic acid derivative. The invention further concerns herbicidal compositions comprising Dicamba and a quinolinyloxy alkanoic acid derivative.

The method of the present invention in particular provides reduced phytotoxicity for monocotylodoneous crop plants, such as maize, sorghum, turf, and cereals, against the damaging effect of Dicamba. Likewise the herbicidal compositions according to present invention comprising Dicamba as herbicidal agent have an improved tolerance in the treated crops.

Dicamba is a well-known pre- and post-emergence herbicide for the selective control of annual and perennial broad-leaved weeds and brush species in cereals, maize, sorghum, sugar cane, asparagus, perennial seed grasses, turf, pastures, rangeland, and non-crop land. Dicamba is preferably applied post-emergence. Dicamba (hereafter Compound I) designates the compound of formula I

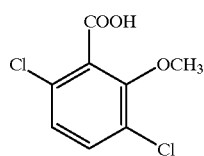

(I)

and salt forms thereof. Dicamba is commercially available under the trademark BANVEL®, and is in practice employed as herbicide in form of the free acid, the sodium salt, potassium salt, dimethylammonium-salt (DMA salt), or diglycolamine salt (DGL salt).

Though Dicamba under normal application conditions provides good selective control of weeds in monocotyledoneous crops, some times when Dicamba is employed at very high dosage rates, e.g. when the weed infection is severe, or unintentionally after wind drift, or by overlapping of spray strips, loss in the treated crops may occur.

One procedure to overcome the above indicated sensitivity responses of plants to Dicamba involves varying the dosage rate. When a reduction in the dosage rate is used to avoid phytotoxicity to the crop plants, reduced weed control is often the result.

Another procedure involves changing the time of application or modifying the ingredients used in the formulations containing the active compound.

With Dicamba these methods have not always achieved the desired result. Therefore there is still a need for a method of avoiding the phytotoxic effects to crop plants.

Surprisingly, it has now been found that the co-application of a quinolinyloxy alkanoic acid derivative and Dicamba at pre- or post-emergence application results in a reduction of the phytotoxic effects of the latter, particularly on grassy (monocotyledoneous) crops such as maize, sorghum, turf, and cereals, without a corresponding reduction of effectiveness in the control of undesired weed plant growth.

This invention therefore concerns a method for reducing phytotoxicity to crop plants due to Dicamba which comprises co-applying to the crop or to the locus thereof Dicamba with a phytotoxicity reducing amount of a quinolyloxy alkanoic acid derivative.

Co-application can be achieved using tank mixes of preformulated individual active ingredients, simultaneous or sequential (preferably 1–2 days) application of such formulations or application of preformulated fixed pre-mix combinations of the individual active ingredients.

The application of the quinolinyloxy alkanoic acid derivatives may also be used as an antagonistic seed treatment when pre- or post-emergence spraying with Dicamba is intended. Such seed treatment will be employed prior to planting of the seeds by application of the quinolinyloxy alkanoic acid derivatives to the locus of the seed, e.g. seed-furrow application, or by seed-dressing according to the routine procedures. The application of the active ingredients may be done to the surface of seeds, e.g. by seed coating, or it may be done by spraying the locus of the seed simultaneously at the time of sowing the crop area with the seeds. The term seed is intended to embrace plant propagating material such as seedlings, seeds, or germinated or soaked seeds.

Quinolinyloxy alkanoic acid derivatives have been described in the literature as herbicide safeners for different herbicides, in particular for herbicidal phenoxyalkanoic acid derivatives, sulfonyl-urea herbicides and chloroacetanilides. Inter alia EP-A-86 750, EP-A-94 349, EP-A-159 290, EPA-191736 and EP-A-492 366 disclose such active compounds, and their utility.

According to the present invention specially the quinolinyloxy alkanoic acid derivatives of formula II

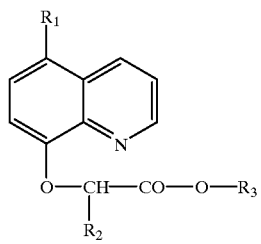

(II)

wherein
  $R_1$ is hydrogen or halogen,
  $R_2$ is hydrogen or $C_{1-4}$ alkyl, and
  $R_3$ is $C_{1-12}$ alkyl, $C_{1-6}$ alkoxy-$C_{1-6}$ alkyl, $C_{3-6}$alkenyloxy-$C_{1-6}$ alky, or $C_{3-6}$alkinyloxy-$C_{1-6}$ alkyl, have exhibited a remarkable capability to reduce the phytotoxicity of Dicamba.

The preferred compounds of formula II are those wherein $R_1$ is halogen, preferably chlorine, $R_2$ is hydrogen or methyl, and $R_3$ is $C_{4-10}$ alkyl, preferably branched alkyl.

Examples for alkyl are methyl, ethyl, propyl, butyl, pentyl, hexyl, heptyl, octyl, nonyl and decyl, including their isomeric forms. Among $C_{4-10}$ alkyl the branched alkyl groups are preferred. Preferred examples of the branched alkyl are isopentyl, 2-ethylhexyl, 2-methylbutyl, 1,1 dimethylpropyl, 2-methylpropyl, 2-methylpentyl, 1-methylpentyl, tert.-butyl, 1-methylhexyl, 1-methylheptyl, 1-methyloctyl, 1-methylnonyl, 2-methylpentyl, 2-methylhexyl, 2-methylheptyl, 2-methyloctyl, 1,3- dimethylpentyl, 1,3-dimethylbutyl, 1,3-dimethylhexyl, and the like, with 1-methylhexyl being most preferred. Examples for alkoxyalkyl are methoxyethyl, ethoxyethyl, or methoxylmethyl. Examples for alkenyloxyalkyl are allyloxyethyl, allyloxypropyl, methallyloxyethyl, or 2-butenyloxyethyl. Examples for aikinyloxy are propargyloxyethyl, or propargyloxypropyl.

However, most preferred among the compounds of formula II is the commercial compound Cloquintocet-mexyl (CGA 185 072), having the chemical designation 1-methylhexyl {(5-chloro-8-quinolinyl)oxy}acetate, hereafter designated as compound IIa. Accordingly, the most preferred embodiments of present invention comprise the method of controlling undesired growth of weeds in mono-cotyledoneous crops by co-employing Dicamba and Cloquintocet-mexyl, and a herbicidal composition comprising Dicamba and Cloquintocet-mexyl as active ingredients.

The application rates of Dicamba and the quinolinyloxy alkanoic acid derivative employed in co-application will of course depend on the quinolinyloxy alkanoic acid derivative chosen, the weeds to be controlled, the crop plant involved, soil type, season, climate, soil ecology, and various other factors. Optimum usage is readily determinable by one skilled in the art using routine testing such as greenhouse or small plot testing. Application rates of Dicamba will usually be those recommended for use of commercially available forms of Dicamba.

In general, for example, satisfactory results are obtained when co-applying at rates of 50 to 2000 g/ha, especially 100 to 1500 g/ha of Dicamba, and 10 to 2000 g/ha, especially 50 to 1500 g/ha of a quinolinyloxy alkanoic acid derivative.

In general, for example, the weight ratio of Dicamba with a quinolinyloxy alkanoic acid derivative lies conveniently within the range of from 1:40 to 200:1, especially 1:15 to 30:1, e.g. 1:3, 1:1.2, 4:1, or 8:1.

A typical co-application of Dicamba (Compound I) with Cloquintocet-mexyl (Compound IIa) would be e.g. from 250 to 1500 g/ha, especially 350 to 1200 g/ha of Compound I and 50 to 1500 g/ha, especially 100 to 1000 g/ha of Compound IIa.

The combinations of the invention are also surprisingly effective when applied to the soil of the crop locus.

When applied to the soil, the quinolinyloxy alkanoic acid derivatives are applied at a rate of 10 to 2000 g/ha, particularly 50 to 1500 g/ha. When applied as a seed dressing the compounds of formula II are applied at a rate of 1.0 to 1000 g, particularly 5 to 800 g, e.g. 300 g, per 100 kg of seed. The amount of Dicamba used as a spray on plants emerging from treated seeds are as given above for co-application purposes.

With co-application of Dicamba and a compound of formula II it is possible to control weeds in crops like cereals. Examples of such weeds are:

| Latin name | English name | Bayer Code |
|---|---|---|
| Amaranthus species | Pigweed | AMASS |
| Anagalis arvensis | Pimpernel, common | ANGAR |
| Bifora radians | | BIFRA |
| Brassica napus ssp. napus | Oil seed rape | BRSNN |
| Calystegia sepium | Bindweed, hedge | CAGSE |
| Capsella bursa-pastoris | Shepherd's purse | CAPBP |
| Centaurea cyanus L. | Knapweed | CENCY |
| Cerastium arvense | Chickweed, Field | CERAR |
| Chenopodium album | Lambsquarters, Common | CHEAL |
| Chenopodium polyspermum | Goosefoot, Manyseeded | CHEPO |
| Cirsium arvense | Thistle, Canada | CIRAR |
| Convolvulus arvensis L. | Bindweed, Field | CONAR |
| Datura stramonium | Jimsonweed | DATST |
| Fumaria officinalis | Fumitory, common | FUMOF |
| Galeopsis tetrahit L. | Hempnettle | GAETE |
| Galinsoga parviflora | Smallflower | GASPA |
| Galium aparine | Cleaver, Bedstraw | GALAP |
| Helianthus annuus L. | Sunflower | HELAN |
| Kochia scoparia | Kochia | KOCSC |
| Lapsana communis | Nippelwort | LAPCO |
| Lithospermum arvense L. | Gromwell, field | LITAR |
| Matricaria chamomilla | Chamomile, wild | MATCH |
| Medicago sativa | Alfalfa | MEDSA |
| Myosotis arvensis | Forgert-me-not, field | MYOAR |
| Papaver rhoeas | Poppy, field | PAPRH |
| Polygonum aviculare | Knotweed, prostrate | POLAV |
| Polygonum convolvulus | Buckwheat, Wild | POLCO |
| Polygonum lapathifolium | Smartweed, Green | POLLA |
| Polygonum persicaria | Ladystumb | POLPE |
| Primula spp. | Primrose | PRISS |
| Ranunculus arvensis | Buttercup | RANAR |
| Rumex obtusifolius[1] | Dock, Broadleaf | RUMOB |
| Salsola pestifer | Thistle, Russian | SASKR |
| Scandix pacten-veneris L. | Venus comb | SCAPV |
| Senecio vulgaris | Groundsel, common | SENVU |
| Silene spp. | Catchfly | SILSS |
| Sinapis arvensis | Mustard, Wild | SINAR |
| Sisymbrium officinale | Mustard, hedge | SSYOF |
| Solanum nigrum | Nightshade, black | SOLNI |
| Solanum sarrachoides | Nightshade, hairy | SOLSA |
| Sonchus arvensis | Sowthistle, Perennial | SONAR |
| Sonchus oleracea | Sowthistle, Annual | SONOL |
| Spergula arvensis | Spurry, corn | SPRAR |
| Stellaria media | Chickweed, Common | STEME |
| Taraxacum officinalis | Dandelion, Common | TAROF |
| Thlaspi arvense | Pennycress, Field (Fanweed, Frenchweed, Stinkweed) | THLAR |
| Trifolium repens | Clover, white | TRFRE |
| Veronica arvensis | Speedwell, corn | VERAR |
| Veronica hederaefolia | Speedwell, Ivyleaf | VERHE |
| Veronica persica | Speedwell, birdeye | VERPE |
| Vicia sp. | Vetch | VICSS |

Co-applied active ingredients when formulated individually or used as preformulated fixed pre-mixes are conveniently employed in association with agriculturally acceptable diluents or carriers.

The advantageous reduction of phytotoxicity is also observed in certain cases where additional herbicidally active ingredients are applied with the mixture of compounds I and II, and even also in cases of synergistic mixtures of Dicamba with other herbicides.

It has now surprisingly been found that biologically active semicarbazone compounds of formula III

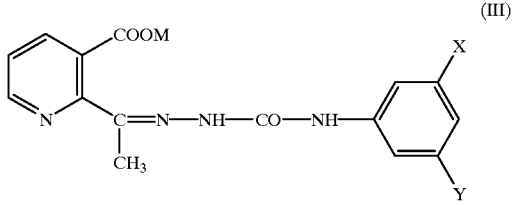

wherein

M is hydrogen, or a salt forming moiety like an alkali metal cation or an optionally substituted ammonium e.g. isopropylammonium, and X and Y represent independent hydrogen, fluorine or chlorine, which form synergistic herbicidal combinations with Dicamba may be employed in the method of the present invention.

A preferred compound of formula III are those wherein M is hydrogen, potassium or sodium, and X and Y are fluorine. For this carboxylic acid and its salts the common name Diflufenzopyr has been proposed. For the purpose of this application Diflufenzopyr will be referred to as Compound IIIa.

The additional component of formula III may be applied together with the components I and II, either in a tank-mix preparation, or as separate sprays, or in a ready-mix formulation which comprises at least one of each components of formulae I, II and III. The weight ratio of component I to component III may vary from 1:100 to 1000:1, preferably 1:10 to 100:1, especially 1:2 to 20:1, e.g. 1:1 to 10:1. Component III is applied at rates of 0.0010 to 1.1 kg/ha preferably 0.010 to 0.55 kg/ha, especially 0.010 to 0.33 kg/ha.

The method applying component III, and three-way-mixtures comprising active ingredients of formulae I, II and III also represent aspects of the present invention.

The composition of the invention may be employed in any conventional form, for example in the form of a twin pack, an instant granulate, a flowable or a wettable powder in combination with agriculturally acceptable adjuvants. Such compositions may be produced in conventional manner, e.g. by mixing and grinding the active ingredients with appropriate adjuvants (diluents and optionally other formulating ingredients such as surfactants).

The term diluent as used herein means any liquid or solid agriculturally acceptable material used to formulate a concentrated material to a usable or desirable strength, including surfactants and carriers, which may be added to the active constituents to bring them in an easier or improved applicable form, respectively, to a usable or desirable strength of activity. For dusts or granules the diluent can be e.g. talc, kaolin or diatomaceous earth, for liquid concentrate forms for example a hydrocarbon such as xylene or an alcohol such as isopropanol, and for liquid application forms e.g. diesel oil or preferably water.

Particularly formulations to be applied in sprayable forms such as water dispersible concentrates or wettable powders may contain surfactants such as wetting and dispersing agents. Surfactant as used herein means an agriculturally acceptable material which imparts emulsifiability, spreading, wetting, dispersibility or other surface-modifying properties. Examples of surfactants are lignin sulfonates, and fatty acid sulfonates, e.g. lauryl sulfonate, the condensation product of formaldehyde with naphthalene sulfonate, an alkylarylsulfonate, an ethoxylated alkylphenol, an ethoxylated fatty alcohol and the like.

A seed dressing formulation is applied in a manner known per se to the seeds employing the quinolinyloxy alkanoic acid derivatives and a diluent in suitable seed dressing formulation form, e.g. as an aqueous suspension or in a dry powder form having good adherence to the seeds. Such seed dressing formulations are known in the art. Seed dressing formulations may contain the quinolinyloxy alkanoic acid derivatives in encapsulated form, e.g. as slow release capsules or microcapsules.

In general, the formulations of combinations of Dicamba and the quinolinyloxy alkanoic acid derivatives include from 0.01 to 90% by weight of active agent(s), from 0 to 20% agriculturally acceptable surfactant and 10 to 99.99% solid or liquid adjuvant(s), the active agent(s) consisting of at least Dicamba together with a quinolinyloxy alkanoic acid derivative. Concentrate forms of compositions generally contain between about 2 and 80%, preferably between about 5 and 70% by weight of active agent. Application forms of formulation may for example contain from 0.01 to 20% by weight, preferably from 0.01 to 5% by weight of active agent.

Useful formulations of the active ingredients either alone or in combination include dusts, granules, suspension concentrates, wettable powders, flowables and the like. They are obtained by conventional manner, e.g. by mixing (an) active ingredient(s) each optionally as twin packs with the diluent(s) and optionally with other ingredients.

Alternatively, the active ingredients may be used in microencapsulated form.

Agriculturally acceptable additives may be employed in the herbicidal compositions to improve the performance of the active ingredient and to reduce foaming, caking and corrosion, for example.

For co-application for example as tank mixes or in sequential treatment commercially available forms of the active ingredients may be employed.

The compositions of the invention can also comprise other compounds having biological activity, e.g. other compounds having a similar or complementary herbicidal or antidotal activity or compounds having fungicidal, insecticidal, or other pesticidal activity.

Solid forms for compositions are preferred from the point of view of environmentally innocuous packaging.

The invention is illustrated by the following examples wherein parts and percentages are by weight and temperatures are in ° C.

EXAMPLE 1

Wettable Powder 60 parts of a mixture of Dicamba (DMA salt, 27.8%) and Cloquintocet-mexyl (72.2%), 1 part sodium alkylnaphthalenesulfonate, 5 parts sodium alkylarylsulfonate-formaldehyde condensate, 5 parts highly disperse silica, and 29 parts kaolin are ground until the particles have the desired size. A 60% wettable powder containing 16.7% of Dicamba and 43.3% of Cloquitocet-mexyl is obtained. The wettable powder is suitable for spray purposes. It is applied as an aqueous suspension by an apparatus suitable for the purpose.

EXAMPLE 2

Seed Dressing Formulation 25 parts of Cloquintocet-mexyl 15 parts of dialkylphenoxypoly(ethylenoxy)ethanol 15 parts of fine silica 44 parts of fine kaolin 0.5 parts of Rhodamine B as a colorant and 0.5 parts of Xanthan Gum are mixed and ground in a contraplex mill at approx. 10'000 rpm to an average particle size of below 20 microns. The resulting formulation is applied to the seeds as an aqueous suspension in an apparatus suitable for that purpose.

EXAMPLE 3

Seed Dressing Formulation

45 Parts of a Cloquintocet-mexyl are mixed with 1.5 parts of diamyl phenoldecaglycolether ethylene oxide adduct, 2 parts of spindle oil, 51 parts of fine talcum and 0.5 parts of colorant Rhodamin B. The mixture is ground in a contraplex mill at 10'000 rpm until an average particle size of less than 20 microns is obtained. The resulting dry powder has good adherence and may be applied to seeds, e.g. by mixing for 2 to 5 minutes in a slowly turning vessel.

EXAMPLE 4

Granules 0.5 Parts by weight of a binder (a non-ionic tenside) are sprayed onto 94.5 parts by weight of quartz sand in a tumbler mixer and thoroughly mixed. 5 Parts by weight of a combination of compounds of formulae I and IIa are then added and thorough mixing continued to obtain a granulate formulation with a particle size in the range from 0.3 to 0.7 mm.

EXAMPLE 5

Post-emergence Test

Active ingredient Compound I is used as aqueous spray prepared from commercial BANVEL 480 SL (DMA-salt of Dicamba). Compound IIa is employed as an aqueous spray prepared from a 10% emulsifiable concentrate or dissolved in a (acetone/methanol/DMF/water, 45:4:1:50 by volume)-mixture (VE-mixture). Dilutions from these stock solutions are performed to allow for preparation of spray solutions consisting of single doses of individual or combined active ingredients. Each dose is applied via a linear track sprayer set to deliver 600 liters/ha spray volume to the foliage of the selected crop/weed seedling species, postemergence application. The seedlings used are cultured to develop plants at the two- to early three-leaf stage. The average plant height at application time is recorded. After application, the treated plants are transferred to the greenhouse and held until termination of the experiment within about three weeks. Plant height and symptoms of injury are recorded twenty days after postemergence application, and the plant new growth is determined as the difference between the plant height at the end of the experiment and the plant height at the time of treatment.

Co-application of Compound I with Compound IIa have been tested in wheat (variety ZENITH), spraying first with the Compound IIa, and after drying with compound I. In the tests the active ingredients were applied to the tested plants alone and in combination with each other. The obtained results were compared to the activity of the herbicide when applied alone. The expected activities of the combination is calculated from the results achieved by the single active ingredients according to the method of Colby (Weeds 15, 1967, pages 20–22) utilizing the following calculation scheme for two-component mixtures:

$$E = 100 - \{(100 - A_m)(100 - B_n)/100\}.$$

In this calculation method for the expected activity of a mixture E is the expected activity of mixture comprising Compound A at rate m Compound B at rate n.

The results were as follows (expressed in % inhibition of the new growth):

TABLE 1

Compound I as BANVEL 480 SL
Compound IIa as emulsifiable concentrate 10%
Assessment 20 days after treatment (% inhibition of new growth)
Wheat variety ZENITH

| Compound I | | Compound IIa g a.i./ha | | | | | | |
|---|---|---|---|---|---|---|---|---|
| | | 30 | | 100 | | 300 | | 1000 |
| g a.i./ha | 0 | expected | found | expected | found | expected | found | expected | found |
| 0 | 0 | | 0 | | 0 | | 0 | | 0 |
| 384 | 31 | 31 | 7 | 31 | 15 | 31 | 30 | 31 | 28 |
| 768 | 67 | 67 | 67 | 67 | 54 | 67 | 53 | 67 | 52 |
| 1152 | 76 | 76 | 70 | 76 | 76 | 76 | 75 | 76 | 71 |

TABLE 2

Compound I as BANVEL 480 SL
Compound IIa as VE-mixture
Assessment 20 days after treatment (% inhibition of new growth)
Wheat variety ZENITH

| Compound I | Compound IIa g a.i./ha | | | | | | | |
|---|---|---|---|---|---|---|---|---|
| | 30 | | 100 | | 300 | | 1000 | |
| g a.i./ha | 0 | expected | found | expected | found | expected | found | expected | found |
| 0 | 0 | | 0 | | 0 | | 0 | |
| 384 | 31 | 31 | 34 | 31 | 39 | 31 | 24 | 31 | 2 |
| 768 | 67 | 67 | 78 | 67 | 75 | 67 | 55 | 67 | 54 |
| 1152 | 76 | 76 | 80 | 76 | 74 | 76 | 68 | 76 | 72 |

EXAMPLE 6

Seed Treatment Test

Seeds of wheat (variety ZENITH) are coated with compound IIa using an experimental seed treatment machinery (Hege 11). Rates per 100 g of seeds are 0.1, 0.3 and 1.0 g a.i.

The treated seeds are planted into flower pots, covered with a layer of soil, and sprayed with an aqueous solution of compound I at rates of 144, 288 and 576 g a.i./ha. Each dose is applied via a linear track sprayer set to deliver 600 liters/ha spray volume to the surface of the planted pots. After application, the treated plants are transferred to the greenhouse and held until termination of the experiment within four weeks. Plant height and visual ratings of plant injury symptoms are recorded twentyeight days after application.

The visual rating of the plant injury and phytotoxicity symptoms is done considering together mainly the plant leaning, the growth inhibition and the plant deformation, and using the following rating scale:

0: no injury/symptoms

1: weak injury/symptoms

2: moderate injury/symptoms

3: strong injury/symptoms

4: very strong injury/symptoms

The following results were obtained:

TABLE 3

Plant injuring and phytotoxicity symptoms
Wheat (ZENITH)
Assessment 28 days after treatment (injury rating)

| Compound I | Compound II (g a.i./100 g seed) | | | |
|---|---|---|---|---|
| g a.i./ha | 0 | 0.1 | 0.3 | 1.0 |
| 0 | 0 | 0.05 | 0.17 | 0.13 |
| 144 | 2.29 | 0.78 | 0.96 | 0.88 |
| 288 | 3.21 | 1.50 | 1.13 | 1.46 |
| 576 | 3.43 | 1.83 | 2.95 | 2.83 |

TABLE 4

Inhibition of plant growth (% of check)
Wheat (ZENITH)
Assessment 28 days after treatment

| Compound I | Compound II (g a.i./100 g seed) | | | |
|---|---|---|---|---|
| g a.i./ha | 0 | 0.1 | 0.3 | 1.0 |
| 0 | 0 | −2 | 10 | −4 |
| 144 | 47 | 8 | 2 | −7 |
| 288 | 67 | 28 | 10 | 4 |
| 576 | 70 | 36 | 57 | 58 |

EXAMPLE 7

Field Tests

On standard field plots sown with spring wheat variety Stephens, located in Idaho, USA (Trial I), the active ingredients Dicamba (Compound I), Cloquintocet-mexyl (Compound IIa), and Diflufenzopyr (Compound IIIa) are applied postemergence at the jointed stage of the wheat with a conventional spray apparatus at usual spray volume and at the given rates. Assessment of the injuring is done visually 51 days after treatment. In another trial with spring wheat variety Penawawa, located in Oregon, USA (Trial II), the active ingredients Dicamba (Compound I), Cloquintocet-mexyl (Compound IIa), and Diflufenzopyr (Compound IIIa) are applied post-emergence at the second node stage of the wheat with a conventional spray apparatus at usual spray volume and at the given rates. The yield of the harvested wheat crop is determined at the end of the growing season, comparing treated and untreated plots.

The following results have been obtained.

| Treatment Compound | application rate g/ha | damage in % Trial I | yield in tons/ha Trial II |
|---|---|---|---|
| Comp I | 560 | 20 | 5.640 |
| Comp IIa | 100 | 2 | 6.200 |
| Comp I+ Comp IIIa | 140+ 56 | 12 | 5.626 |
| Comp I+ Comp IIa | 560+ 100 | 2 | 6.321 |
| Comp I+ Comp IIIa+ Comp IIa | 140+ 56+ 100 | 2 | 6.753 |
| untreated Control | — | 0 | 6.753 |

What is claimed is:

1. A method for reducing phytotoxicity of Dicamba to crop plants, which comprises co-applying to the crop plants or to the locus thereof a phytotoxicity reducing effective amount of a quinolinyloxy alkanoic acid derivative together with a herbicidally effective amount of Dicamba of formula I

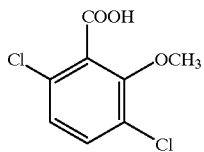
(I)

and salt forms thereof; and wherein said quinolinyloxy alkanoic acid derivative is selected from the compounds of formula II

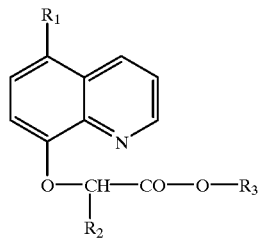
(II)

wherein $R_1$ is hydrogen or halogen, $R_2$ is hydrogen or $C_{1-4}$alkyl, and $R_3$ is $C_{1-12}$alkyl, $C_{1-6}$alkoxy-$C_{1-6}$alkyl, $C_{3-6}$alkenyloxy-$C_{1-6}$alkyl, or $C_{3-6}$alkinyloxy-$C_{1-6}$alkyl; and wherein said Dicamba is applied in an amount from 50 to 2000 g/ha; and wherein said quinolinyloxy alkanoic acid derivative is applied in an amount from 10 to 2000 g/ha.

2. A method according to claim 1 wherein the quinolinyloxy alkanoic acid derivative is Cloquintocet-mexyl.

3. A method according to claim 1 wherein additionally a compound of formula III

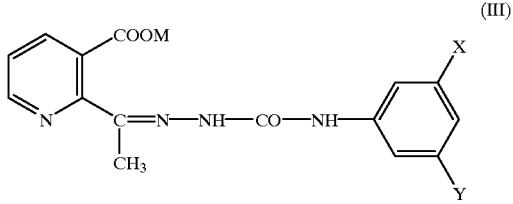
(III)

wherein

M is hydrogen, or a salt forming moiety, and X and Y represent independent hydrogen, fluorine or chlorine, is applied with the combination of compounds of formulae I and II.

4. A method according to claim 3, wherein the compound of formula III is Diflufenzopyr.

5. A method of selectively controlling unwanted plant growth in monocotyledoneous crops which comprises co-application to the locus of said unwanted plant growth an herbicidally effective amount of Dicamba and salt forms thereof, and a phytotoxicity reducing effective amount of a quinolinyloxy alkanoic acid derivative; and wherein said quinolinyloxy alkanoic acid derivative is selected from the compounds of formula II

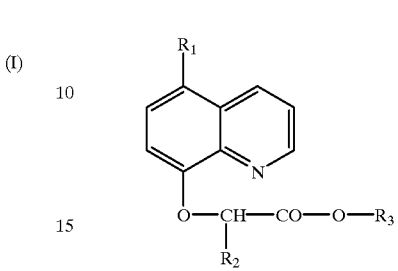
(II)

wherein $R_1$ is hydrogen or halogen, $R_2$ is hydrogen or $C_{1-4}$alkyl, and $R_3$ is $C_{1-12}$alkyl, $C_{1-6}$alkoxy-$C_{1-6}$alkyl, $C_{3-6}$alkenyloxy-$C_{1-6}$alkyl, or $C_{3-6}$alkinyloxy-$C_{1-6}$alkyl; and wherein said Dicamba is applied in an amount from 50 to 2000 g/ha; and wherein said quinolinyloxy alkanoic acid derivative is applied in an amount from 10 to 2000 g/ha.

6. A method according to claim 5 wherein the quinolinyloxy alkanoic acid derivative is Cloquintocet-mexyl.

7. A method according to claim 5 wherein additionally a compound of formula III

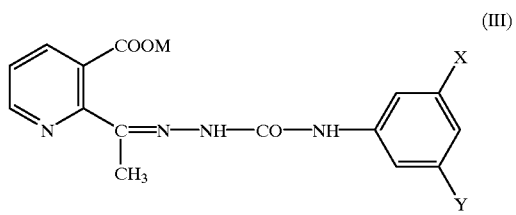
(III)

wherein

M is hydrogen, or a salt forming moiety, and X and Y represent independent hydrogen, fluorine or chlorine, is applied with the combination of said dicamba and said quinolinyloxy alkanoic acid derivative.

8. A method according to claim 7, wherein the compound of formula III is Diflufenzopyr.

9. A herbicidal composition comprising a herbicidally effective aggregate amount of dicamba and salt forms thereof, and of phytotoxicity reducing effective amount of a quinolinyloxy alkanoic acid derivative; and wherein said quinolinyloxy alkanoic acid derivative is selected from the compounds of formula II

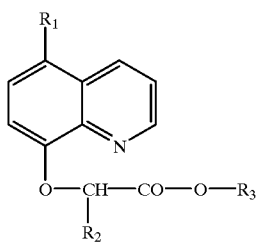

(II)

wherein

R$_1$ is hydrogen or halogen,

R$_2$ is hydrogen or C$_{1-4}$alkyl, and

R$_3$ is C$_{1-12}$alkyl, C$_{1-6}$alkoxy-C$_{1-6}$alkyl, C$_{3-6}$alkenyloxy-C$_{1-6}$alkyl, or C$_{3-6}$alkinyloxy-C$_{1-6}$alkyl; and wherein the weight ratio of said Dicamba to said quinolinyloxy alkanoic acid derivative is in the range of 1:40 to 200:1.

10. A herbicidal composition according to claim 9 wherein the quinolinyloxy alkanoic acid derivative is Cloquintocet-mexyl.

11. A herbicidal composition comprising a herbicidally effective aggregate amount of Dicamba and salt forms thereof, and of a semicarbazone compound and of phytotoxicity reducing effective amount of a quinolinyloxy alkanoic acid derivative; and wherein said quinolinyloxy alkanoic acid derivative is selected from the compounds of formula II

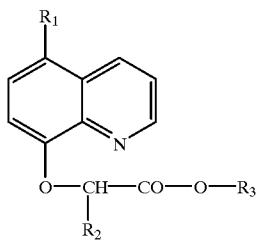

(II)

wherein

R$_1$ is hydrogen or halogen,

R$_2$ is hydrogen or C$_{1-4}$alkyl, and

R$_3$ is C$_{1-12}$alkyl, C$_{1-6}$alkoxy-C$_{1-6}$alkyl, C$_{3-6}$alkenyloxy-C$_{1-6}$alkyl, or C$_{3-6}$alkinyloxy-C$_{1-6}$alkyl; and wherein the weight ratio of said Dicamba to said quinolinyloxy alkanoic acid derivative is in the range of 1:40 to 200:1, and the weight ratio of said Dicamba to the said semicarbazone compound is in the range of 1:100 to 1000:1.

12. A herbicidal composition according to claim 11 wherein the semicarbazone is selected from the compounds of formula III

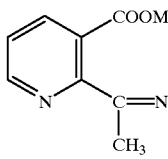

(III)

wherein

M is hydrogen, or a salt forming moiety, and X and Y represent independent hydrogen, fluorine or chlorine.

13. A herbicidal composition according to claim 11 wherein the quinolinyloxy alkanoic acid derivative is Cloquintocet-mexyl.

14. A herbicidal composition according to claim 11 wherein the semicarbazone compound is Diflufenzopyr.

15. A method for reducing phytotoxicity of Dicamba to crop plants, which comprises co-applying to the crop plants or to the locus thereof a phytotoxicity reducing effective amount of a quinolinyloxy alkanoic acid derivative together with a herbicidally effective amount of Dicamba of formula I

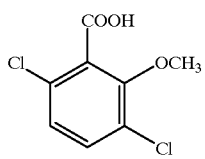

(I)

and salt forms thereof; and wherein said quinolinyloxy alkanoic acid derivative is selected from the compounds of formula II

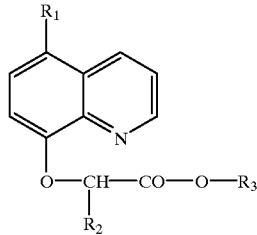

(II)

wherein

R$_1$ is hydrogen or halogen,

R$_2$ is hydrogen or C$_{1-4}$alkyl, and

R$_3$ is C$_{1-12}$alkyl, C$_{1-6}$alkoxy-C$_{1-6}$alkyl, C$_{3-6}$alkenyloxy-C$_{1-6}$alkyl, or C$_{3-6}$alkinyloxy-C$_{1-6}$alkyl; and wherein said quinolinyloxy alkanoic acid derivative is applied as a seed dressing; and wherein the application rate of said quinolinyloxy alkanoic acid derivative is from 1.0 to 1000 g per 100 kg of seeds.

16. A method of selectively controlling unwanted plant growth in monocotyledoneous crops which comprises co-application to the locus of said unwanted plant growth an herbicidally effective amount of Dicamba and salt forms thereof and a phytotoxicity reducing effective amount of a quinolinyloxy alkanoic acid derivative; and wherein said quinolinyloxy alkanoic acid derivative is selected from the compounds of formula II

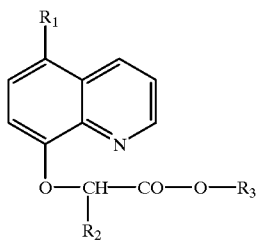

(II)

wherein

R$_1$ is hydrogen or halogen,

R$_2$ is hydrogen or C$_{1-4}$alkyl, and

R$_3$ is C$_{1-12}$alkyl, C$_{1-6}$alkoxy-C$_{1-6}$alkyl, C$_{3-6}$alkenyloxy-C$_{1-6}$alkyl, or C$_{3-6}$alkinyloxy-C$_{1-6}$alkyl; and wherein said quinolinyloxy alkanoic acid derivative is applied as a seed dressing, and wherein the application rate of said quinolinyloxy alkanoic acid derivative is from 1.0 to 1000 g per 100 kg of seeds.

* * * * *